(12) United States Patent     (10) Patent No.: US 8,911,341 B2
Brunson et al.     (45) Date of Patent: Dec. 16, 2014

(54) HYPODERMIC NEEDLE CONTAINMENT SYSTEM

(76) Inventors: Robert W. Brunson, Ogden, UT (US); Jeremy Sorensen, West Jordan, UT (US)

(*) Notice: Subject to any disclaimer, the term of this patent is extended or adjusted under 35 U.S.C. 154(b) by 44 days.

(21) Appl. No.: 13/551,550

(22) Filed: Jul. 17, 2012

(65) Prior Publication Data

US 2014/0024878 A1     Jan. 23, 2014

(51) Int. Cl.
    *B65D 85/24*     (2006.01)
    *A61B 19/02*     (2006.01)

(52) U.S. Cl.
    CPC ................... *A61B 19/0288* (2013.01)
    USPC ....................... 588/249.5; 588/252

(58) Field of Classification Search
    CPC .................................................. A61B 19/0288
    USPC .......................................................... 588/255
    See application file for complete search history.

(56) References Cited

U.S. PATENT DOCUMENTS

| | | | | |
|---|---|---|---|---|
| 5,046,614 A | * | 9/1991 | Torres et al. | 206/366 |
| 5,172,808 A | * | 12/1992 | Bruno | 206/366 |
| 5,273,221 A | * | 12/1993 | McCarthy | 241/99 |
| 5,419,435 A | * | 5/1995 | Perzan et al. | 206/366 |
| 6,010,444 A | * | 1/2000 | Honeycutt et al. | 588/255 |
| 2005/0106087 A1 | * | 5/2005 | Tanhehco | 423/1 |

* cited by examiner

*Primary Examiner* — John Kreck
(74) *Attorney, Agent, or Firm* — Michael F. Krieger; Kirton McConkie

(57) ABSTRACT

Containment systems and methods safely and permanently encapsulate a sharp portion of a sharp medical instrument (e.g. a hypodermic needle). The containment system includes a cap or other container having a rim defining an open end configured to receive the sharp portion therein and an ingress port configured to permit injection of a liquid hardenable solution into the container to encapsulate the sharp portion. The method of use includes inserting the sharp metal instrument into the container, and injecting a liquid hardenable solution into the container through the ingress port to encapsulate the sharp portion of the medical instrument. The hardenable solution then hardens, encapsulating the sharp portion of the medical instrument. The liquid hardenable solution is injected by a base or base unit configured to receive the container and to inject the solution through the ingress port.

17 Claims, 7 Drawing Sheets

HYPODERMIC NEEDLE CONTAINMENT SYSTEM

BACKGROUND OF THE INVENTION

1. Field of the Invention

The present invention relates to containment systems for hypodermic needles and other sharp medical instruments, and more particularly to containment systems permanently encapsulating and containing hypodermic needles to prevent reuse and accidental needle sticks.

2. Background and Related Art

The handling and disposal of used medical instruments, particularly sharp medical instruments such as hypodermic needles, suture needles, lancets, trocars, scalpel blades and the like is a major problem facing healthcare professionals. Blood-born pathogens can be easily transmitted by inadvertent contact with the used medical instrument such as by accidental needle sticks.

In order to avoid such accidental needle sticks, especially immediately after using the needle, the healthcare professional will attempt to cover the needle with a protective cap or sheath so that the instrument can be safely transported for disposal. The provision for caps and sheaths affords some degree of protection, however many accidental needle sticks occur while trying to place the cap or sheath back on the needle in preparation for transport for disposal.

In the absence of re-capping or re-sheathing, quite often the used medical instrument is transported uncovered to a sharps container which ideally is located proximate to the site. The sharps container holds several used medical instruments in a hard puncture-resistant package which is subsequently collected for final disposal. However, this still requires the healthcare professional to handle and transport the unprotected needle after use. Also, the collected used instruments remain on site in the sharps container until collected for final disposal.

The art has seen many devices for capping, closing and sheathing used sharp medical instruments for disposal. Many of these devices simply enclose the entire medical instrument, or at least the sharp portion thereof in a protective enclosure. Other of these devices attempt to encapsulate or surround the used medical instrument with a composition which hardens around the sharp portion of the instrument, providing permanent containment and protection.

One such encapsulation system uses a two-part hardenable compound provided in a container (e.g. a needle cover) which accepts a sharp medical instrument such as a hypodermic needle. The container supports a hardenable resin such as a cyanoacrylate ester and a filler of particulate matter in spaced separation. The filler includes an accelerator which is used to speed up the hardening of the resin. The resin and the filler accelerator are separated by a rupturable partition such as thin glass. The used medical instrument, such as a needle, is inserted into the container, rupturing the glass membrane between the two components, thereby causing the components to come together and harden around the needle.

Such encapsulation systems have several disadvantages. First, it can be difficult and hence expensive to properly manufacture such systems, as the small scale of such systems necessitates care and precision in manufacturing. If any manufacturing deficiencies allow the two-part hardenable compound to mix before the intended time, the attempt to insert the needle into the encapsulation system may fail, and an additional system will be needed. Additionally, such systems, of necessity require two separate devices for protecting the hypodermic needle before and after use: a standard cap or cover for protecting the needle before use, and an encapsulation cap or cover for after use of the needle. The use of multiple caps or covers results in extra waste, extra costs, extra time spent seeking to ensure that the correct cap or cover is used, etc. Finally, such systems may be prone to inadequate mixing of the two-part hardenable compound, such that permanent encapsulation of the needle is not achieved.

BRIEF SUMMARY OF THE INVENTION

Implementation of the invention provides containment systems for encapsulating a sharp medical instrument. The containment system may include a container having a rim defining an open end configured to receive a sharp portion of the medical instrument and an ingress port configured to permit injection of a liquid hardenable solution into the container to encapsulate a sharp portion of the medical instrument. The sharp medical instrument may be a hypodermic needle.

The container may also include a compound disposed on an interior surface of the container, the compound being configured to cause hardening of the liquid hardenable solution. The container may also include baffles disposed on an interior surface of the container to facilitate mixing of the liquid hardenable solution. The ingress port may be disposed on one of a side of the container, a side of the container distal the rim, and an end of the container distal the rim.

The ingress port may be one of a pair of ingress ports. Each of the ingress ports may be located on opposite sides of the container substantially equally distal the rim. The pair of ingress ports may be configured to permit separate components of the liquid hardenable solution to be injected into the container and mixed therein.

The containment system may also include a base, the base having a recess configured to receive at least a portion of the container distal the rim therein, an actuator configured to be contacted by an end of the container distal the rim and to be displaced by continued insertion of the container into the recess, and an injection system configured to inject the liquid hardenable solution into the container upon displacement of the actuator.

Implementation of the invention also provides methods for safely and permanently encapsulating a sharp medical instrument. The method includes inserting the sharp metal instrument into a container, the container having a rim defining an open end configured to receive a sharp portion of the medical instrument and an ingress port. The method also includes injecting a liquid hardenable solution into the container through the ingress port to encapsulate the sharp portion of the medical instrument.

The method may also include inserting the container into a base, wherein the base injects the liquid hardenable solution into the container containing the sharp portion of the medical instrument. In some instances, the container is first inserted into the base, and the sharp portion of the medical instrument is then inserted into the container within the base. In other instances, the sharp portion of the medical instrument is first inserted into the container, and the container containing the sharp portion of the medical instrument is then inserted into the base.

The base may inject the liquid hardenable solution when the container containing the sharp medical instrument is depressed farther into the base than the initial insertion distance of the container. The force of depressing the container may inject the liquid hardenable solution.

Implementation of the invention also provides a containment system for encapsulating a hypodermic needle. The system includes a cap having a rim defining an open end configured to receive the hypodermic needle and an ingress port, the ingress port being configured to permit injection of a liquid hardenable solution into the cap to encapsulate the hypodermic needle.

The cap may include a compound disposed on an interior surface of the cap, the compound being configured to cause hardening of the liquid hardenable solution. The cap may also include baffles disposed on an interior surface of the cap to cause mixing of the liquid hardenable solution during injection of the solution.

The ingress port may be one of a pair of ingress ports. Each of the ingress ports may be located on opposite sides of the cap substantially equally distal the rim. The pair of ingress ports may be configured to permit separate components of the liquid hardenable solution to be injected into the cap and mixed therein.

The containment system may also include a base having a recess configured to receive at least a portion of the cap distal the rim therein, an actuator configured to be contacted by an end of the cap distal the rim and to be displaced by continued insertion of the cap into the recess, and an injection system configured to inject the liquid hardenable solution into the cap upon displacement of the actuator.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
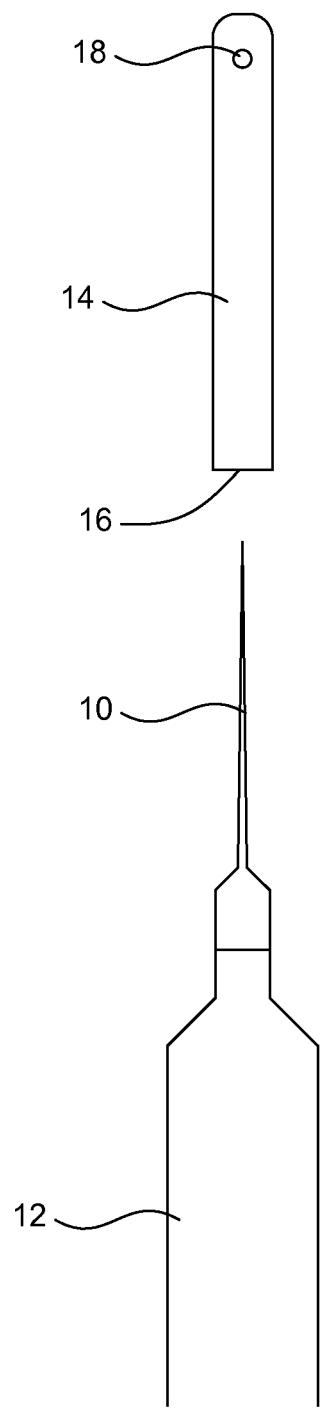
FIG. 1 shows a plan view of a representative hypodermic needle and cap.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention provide containment systems for encapsulating a sharp medical instrument. The containment system may include a container having a rim defining an open end configured to receive a sharp portion of the medical instrument and an ingress port configured to permit injection of a liquid hardenable solution into the container to encapsulate a sharp portion of the medical instrument. The sharp medical instrument may be a hypodermic needle.

The container may also include a compound disposed on an interior surface of the container, the compound being configured to cause hardening of the liquid hardenable solution. The container may also include baffles disposed on an interior surface of the container to facilitate mixing of the liquid hardenable solution. The ingress port may be disposed on one of a side of the container, a side of the container distal the rim, and an end of the container distal the rim.

The ingress port may be one of a pair of ingress ports. Each of the ingress ports may be located on opposite sides of the container substantially equally distal the rim. The pair of ingress ports may be configured to permit separate components of the liquid hardenable solution to be injected into the container and mixed therein.

The containment system may also include a base, the base having a recess configured to receive at least a portion of the container distal the rim therein, an actuator configured to be contacted by an end of the container distal the rim and to be displaced by continued insertion of the container into the recess, and an injection system configured to inject the liquid hardenable solution into the container upon displacement of the actuator.

At least some embodiments of the invention also provide methods for safely and permanently encapsulating a sharp medical instrument. The method includes inserting the sharp metal instrument into a container, the container having a rim defining an open end configured to receive a sharp portion of the medical instrument and an ingress port. The method also includes injecting a liquid hardenable solution into the container through the ingress port to encapsulate the sharp portion of the medical instrument.

The method may also include inserting the container into a base, wherein the base injects the liquid hardenable solution into the container containing the sharp portion of the medical instrument. In some instances, the container is first inserted into the base, and the sharp portion of the medical instrument is then inserted into the container within the base. In other instances, the sharp portion of the medical instrument is first inserted into the container, and the container containing the sharp portion of the medical instrument is then inserted into the base.

The base may inject the liquid hardenable solution when the container containing the sharp medical instrument is depressed farther into the base than the initial insertion distance of the container. The force of depressing the container may inject the liquid hardenable solution.

Some embodiments of the invention provide a containment system for encapsulating a hypodermic needle. The system includes a cap having a rim defining an open end configured to receive the hypodermic needle and an ingress port, the ingress port being configured to permit injection of a liquid hardenable solution into the cap to encapsulate the hypodermic needle.

The cap may include a compound disposed on an interior surface of the cap, the compound being configured to cause hardening of the liquid hardenable solution. The cap may also include baffles disposed on an interior surface of the cap to cause mixing of the liquid hardenable solution during injection of the solution.

The ingress port may be one of a pair of ingress ports. Each of the ingress ports may be located on opposite sides of the cap substantially equally distal the rim. The pair of ingress ports may be configured to permit separate components of the liquid hardenable solution to be injected into the cap and mixed therein.

The containment system may also include a base having a recess configured to receive at least a portion of the cap distal the rim therein, an actuator configured to be contacted by an end of the cap distal the rim and to be displaced by continued insertion of the cap into the recess, and an injection system configured to inject the liquid hardenable solution into the cap upon displacement of the actuator.

While embodiments of the invention will be discussed with reference to a cap for a hypodermic needle, the discussion is intended to be illustrative of any applicable container for containing a sharp portion of any sharp medical instrument, where the medical instrument is not limited to a hypodermic needle. Therefore, the principles discussed herein may be applied to alternative devices and systems for use with any such medical instruments.

FIG. 1 illustrates one system for encapsulating a sharp portion of a sharp medical instrument, namely a hypodermic needle 10 affixed to a syringe 12. The needle 10 and syringe 12 are in all respects essentially identical to known syringes and needles, and permit delivery of liquids from the syringe 12 through a hollow channel of the needle 10 into a target tissue, vessel, etc. As with any needle, it is desirable to prevent accidental needle sticks of the needle 10 before and after the needle 10 is to be used, and it is also desirable to prevent re-use of the needle 10 after its initial intended use to prevent the spread of blood-borne pathogens and the like. It is also desirable to prevent re-use of the needle 10, as re-use is commonly associated with illicit drug use, and is therefore even more likely to be associated with pathogen transmission.

Therefore, associated with the needle 10 and the syringe 12 is a cap 14, which is one example of a container for receiving a sharp portion of a sharp medical instrument. As with standard syringe caps, the cap 14 is sized and formed so as to be removably affixable to the syringe 12 covering the needle 10. The cap 14 may be affixable to the syringe 12 using any known system or method, including a snap fit, a frictional engagement, or a threaded engagement between the cap 14 and the syringe 12.

The cap 14 may be constructed essentially similar to known caps, covers, and containers for syringes, and may be made, for example, of a hard plastic material. The cap 14 may typically be provided covering the needle 10, either with the syringe 12 or as a needle system to be affixed to the syringe 12, as is typically done with existing needle and cap or needle, syringe and cap systems. Thus, embodiments of the invention may be advantageously used in conjunction with existing needles and syringes in all respects without modification to the existing needles and syringes.

The cap 14 includes a rim 16 defining an open end of the cap 14, the open end being configured to receive the needle 10 into the cap 14. The cap 14 also includes at least one ingress port 18, as shown in FIG. 1. The presence of the ingress port 18 differentiates the cap 14 from existing caps, which are typically substantially solid, or at least do not include a feature designed for introducing a liquid hardenable solution into the caps. The ingress port 18 permits a liquid hardenable solution to be injected into the cap, where the solution hardens around the needle 10, safely and permanently encapsulating the needle 10 and preventing accidental needle sticks and undesirable reuse of the needle 10. While the ingress port 18 may be located at any location on the cap 14 that permits encapsulation of the needle 10, such as in the side or distal end of the cap 14, in at least some embodiments the ingress port 18 is located distal the rim 16 as shown in FIG. 1, so as to be located proximate the sharp portion of the needle 10 and to better ensure that the sharp portion of the needle 10 is surrounded by the hardenable solution on injection of the solution.

Figure 2:
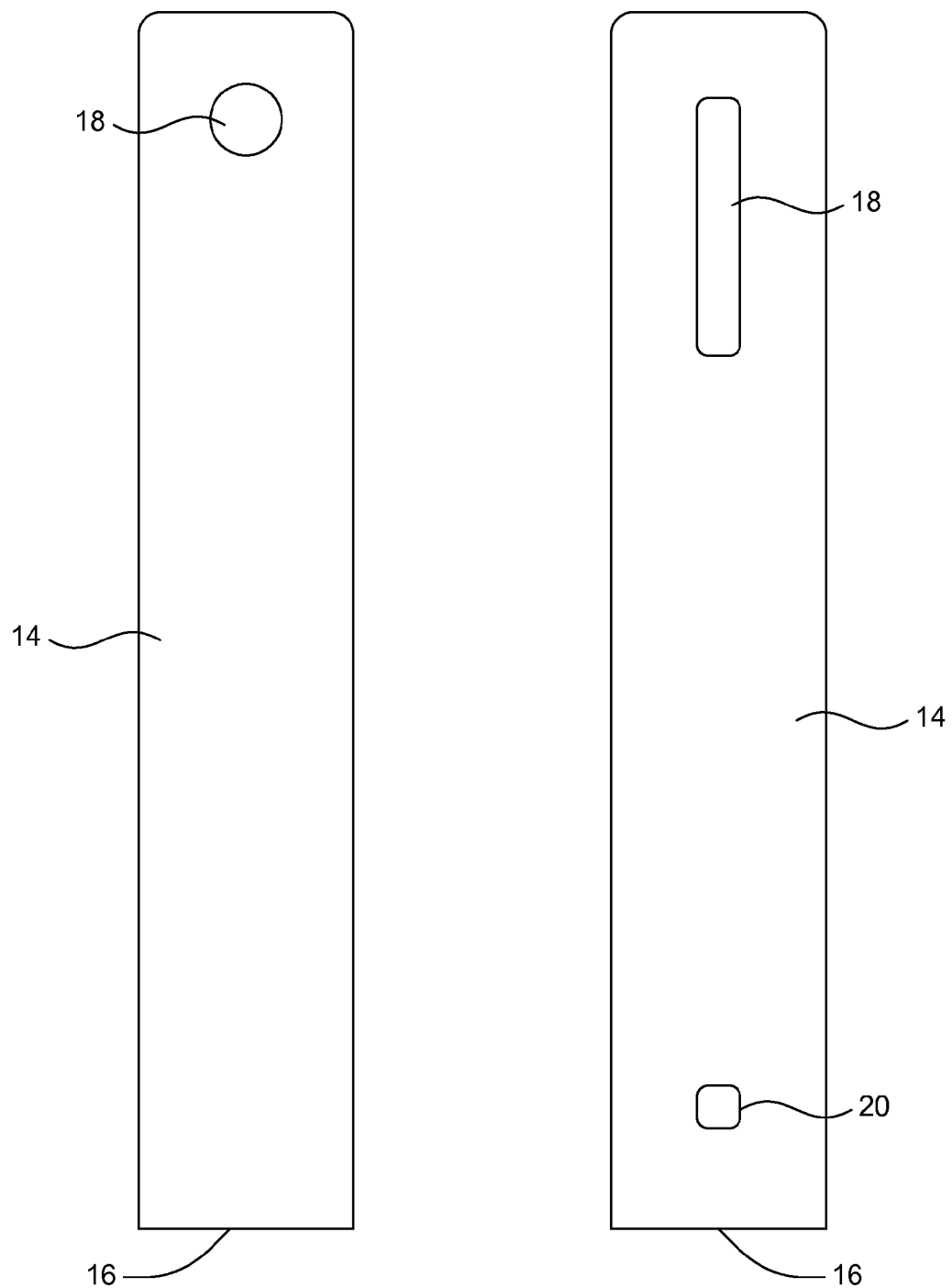
FIG. 2 shows a plan view of two representative caps.

As illustrated in FIG. 2, which shows two alternate embodiments of the cap 14 side by side, the ingress port 18 may be of essentially any shape and size that permits injection of the hardenable solution. In at least some embodiments, the ingress port 18 may be sized and shaped to minimize outflow of the hardenable solution from the ingress port 18 after injection and before the hardenable solution has hardened within the cap 14. To facilitate injection of the hardenable solution into the cap 14, the cap 14 may also include one or more vent ports 20 distal the ingress port 18 to permit outflow of air from the cap 14 as the hardenable solution is injected into the cap 14.

Figure 3:
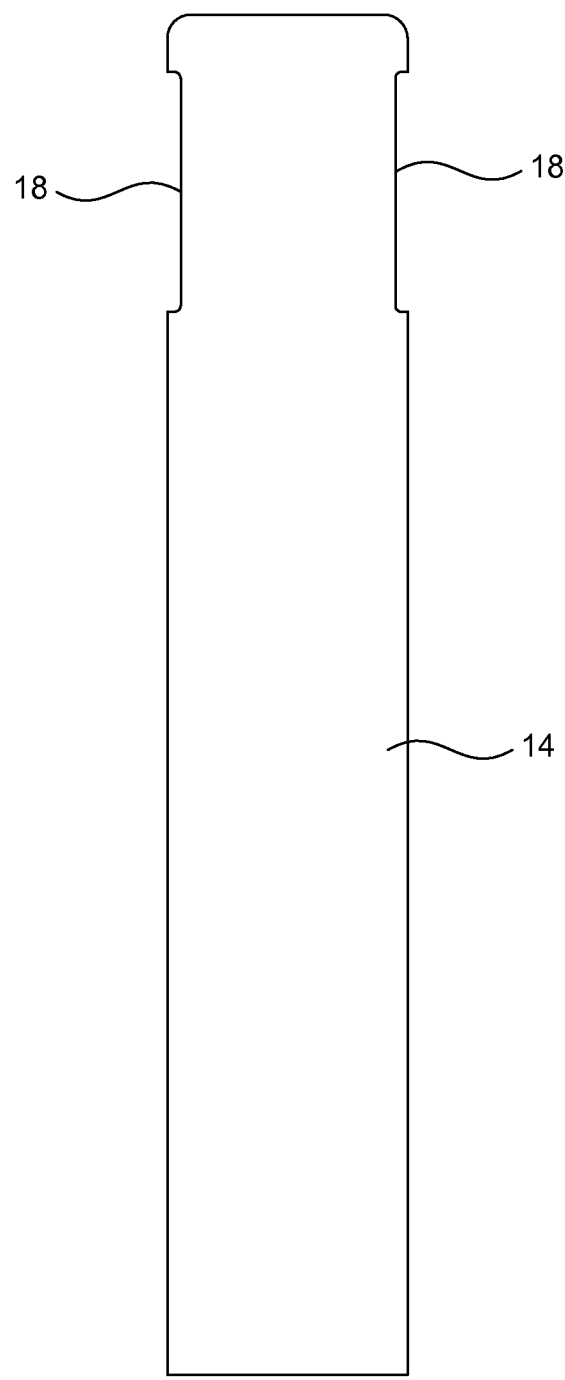
FIG. 3 shows a rotated plan view of a representative cap.

FIG. 3 shows a side view of another embodiment of the cap 14. In this embodiment, the cap 14 includes two ingress ports 18 located on opposite sides of the cap 14. In such an embodiment, one of the ingress ports 18 is used to inject one component of the liquid hardenable solution, while the other ingress port 18 is used to inject the other component of the liquid hardenable solution. The two components of the solution mix within the cap, which, as is known in the hardenable solution art, initiates a reaction causing the hardenable solution to harden. As the needle 10 is disposed in the middle of the cap 14, it is essentially located at the boundary between the two components, such that mixing of the two components of the hardenable solution is most complete at the critical location of the needle 10.

Figure 4:
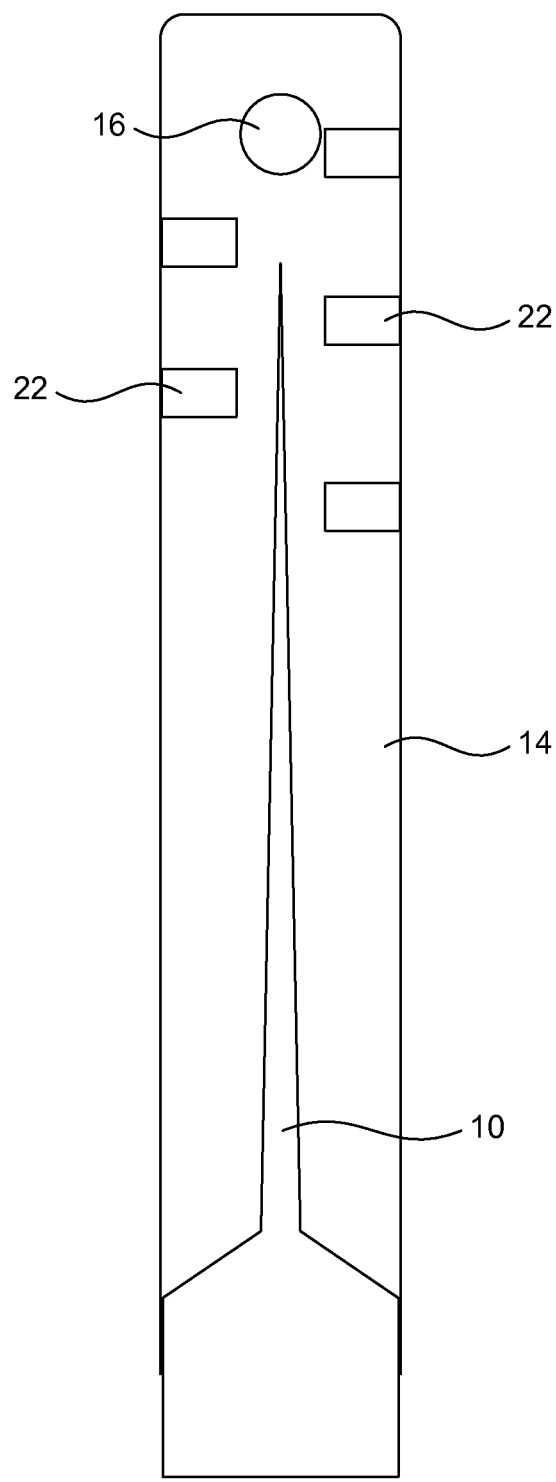
FIG. 4 shows a cross-sectional view of a representative hypodermic needle inserted into a representative cap.

In some embodiments, however, such as illustrated in FIG. 4, additional features such as one or more baffles 22 located on an interior surface of the cap 14 may be used to further ensure mixing of the two components of the liquid hardenable solution. In other embodiments, one of the components of the liquid hardenable solution may be pre-disposed on an interior surface of the cap 14 (or a portion thereof), such that only one component of the liquid hardenable solution is injected into the cap 14, and in such embodiments the number of ingress ports 18 may optionally be reduced to one.

Figure 5:
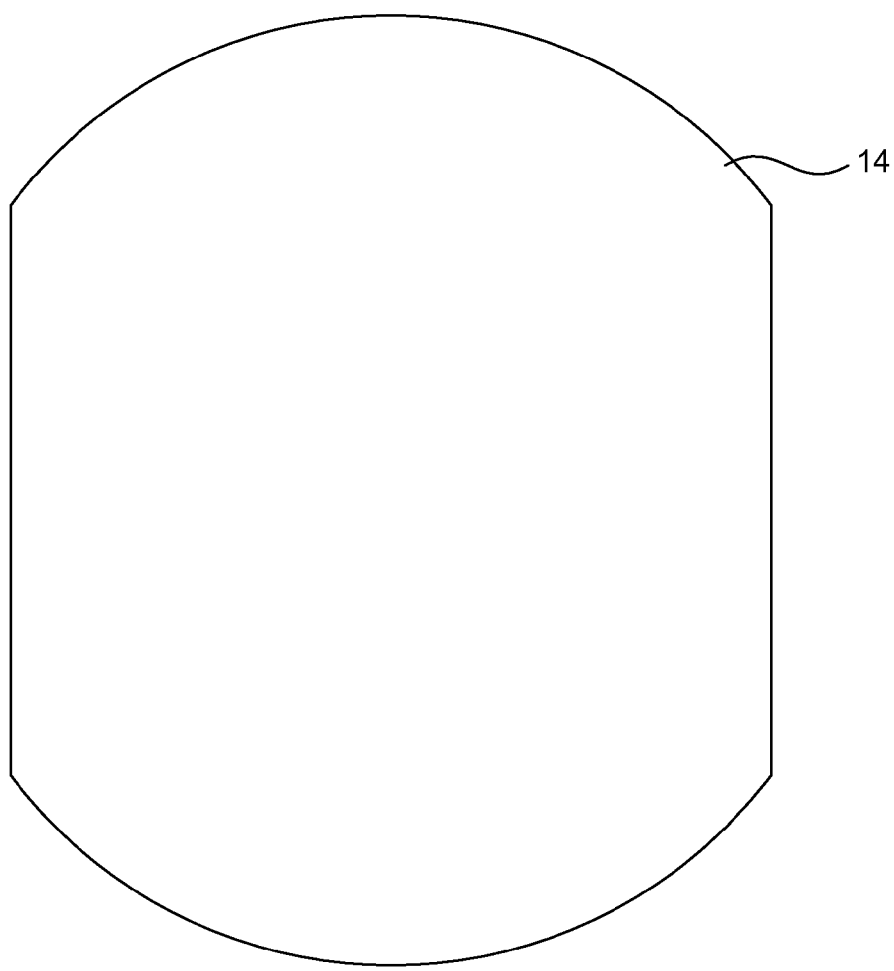
FIG. 5 shows a top view of a representative cap.

Since the ingress ports 18 of the cap 14 are used to introduce the liquid hardenable solution into the interior of the cap 14, it is desirable to ensure that the system or component used to inject or otherwise introduce the liquid hardenable solution properly aligns with and/or engages the ingress port 18 or ports 18. Therefore, the cross-sectional shape of the distal end of the cap 14 may be shaped so as to only permit injection when the cap 14 is properly aligned. This is illustrated by FIG. 5, which shows an end or top view of the distal end of the cap 14, showing how the sides are flattened such that the cap 14 may be properly aligned as discussed.

Figure 6:
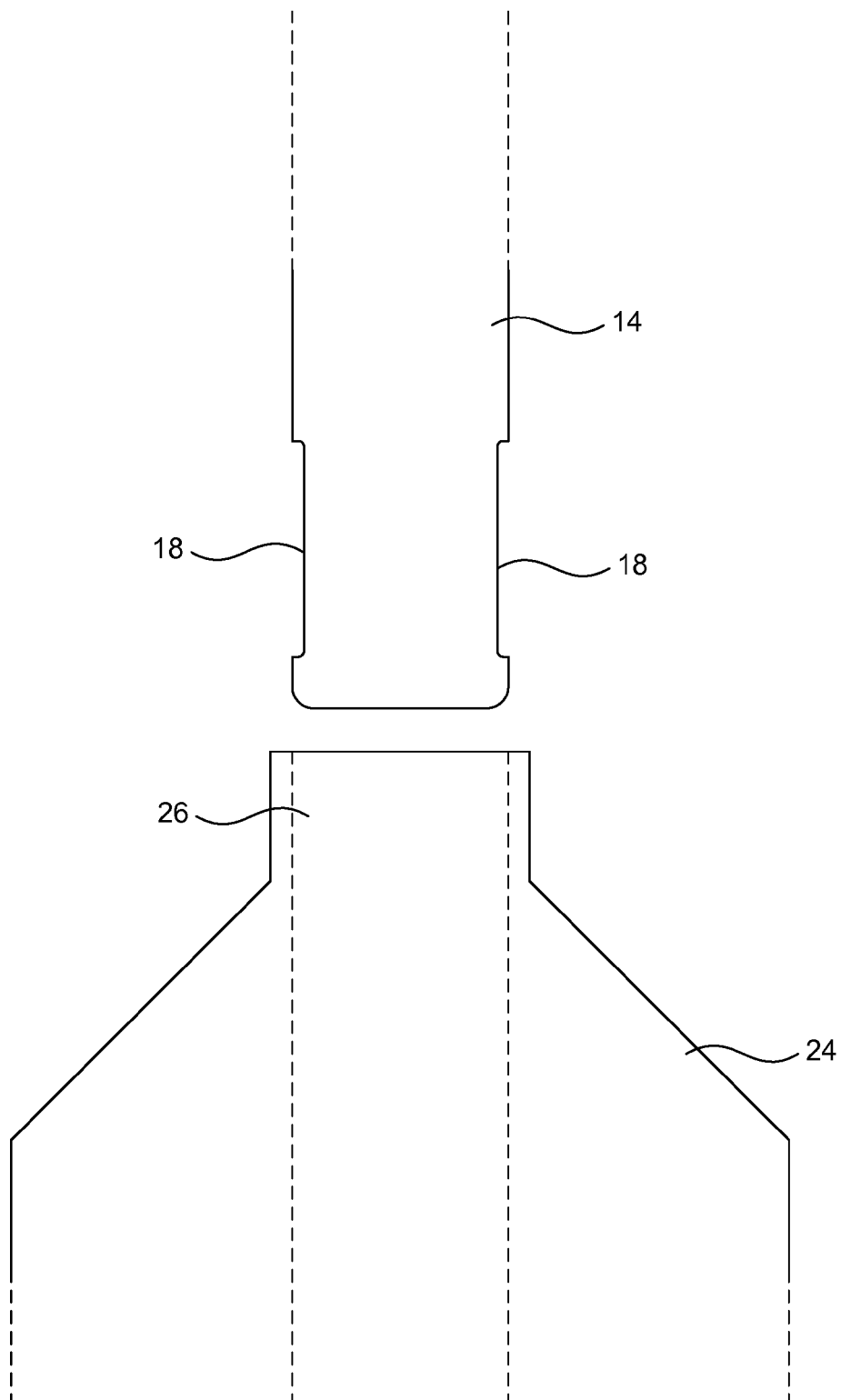
FIG. 6 shows a plan view of a cap just prior to insertion into a base unit.

FIG. 6 shows a side view of a base 24 or base unit into which the cap 14 is to be inserted for injection of the liquid hardenable solution. The base 24 includes a recess 26 that is sized and shaped to receive the cap 14 therein, including being shaped to ensure alignment of the ingress ports 18 with the components of the base 24 configured to inject one or more components of the liquid hardenable solution.

Figure 7:
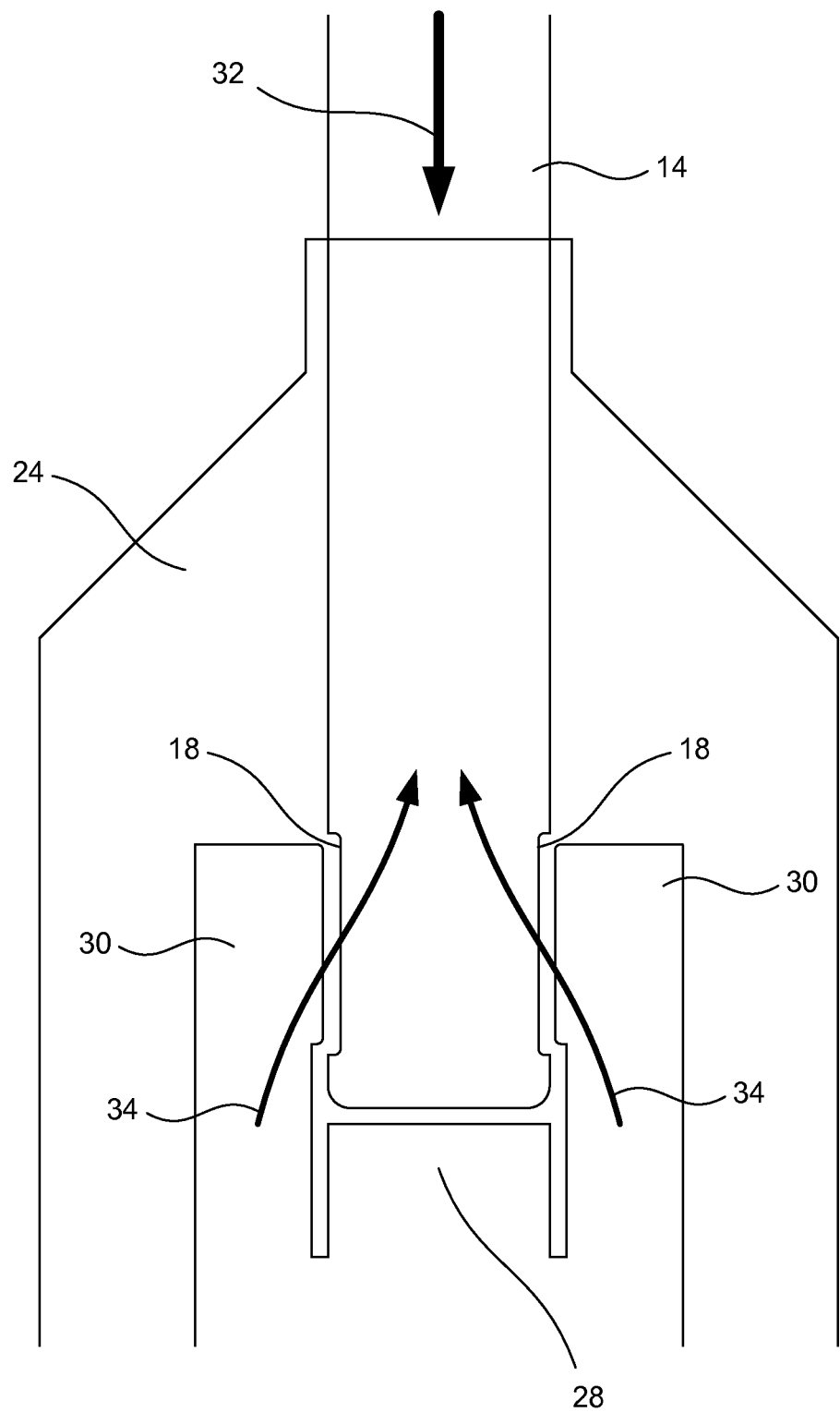
FIG. 7 shows a sectional view of a cap inserted into a base unit.

In use, the cap 14 is inserted into the recess 26 of the base 24, as shown in FIG. 7, until the distal end of the cap 14 contacts and engages an actuator 28. When the cap 14 is inserted in the recess 26 and the distal end of the cap is contacting the actuator 28, the ingress ports 18 are aligned with an injection system 30 of the base 26, as shown in FIG. 7. The cap 14 may be inserted into this position either with the needle 10 contained therein or before the needle 10 has been inserted into the cap 14. Regardless, once the needle 10 is within the cap 14 and injection of the liquid hardenable solution is desired, the cap 14 is further depressed in the recess in the direction of arrow 32, which causes displacement of the actuator 28, which causes the injection system 30 to inject liquid hardenable solution into the cap 14 in the direction of flow of arrows 34. The injection may be caused by the pressure of further insertion of the cap 14, as with a pumping action, or insertion past a certain point may activate a separately-controlled system to inject a proper amount of liquid hardenable solution.

As may be appreciated, the use of the base 24 and the reception of the cap 14 to the recess 26 of the base facilitates better avoidance of accidental needle sticks. Although the cap 14 can be used traditionally, with the user capping the needle 10 by hand after use of the needle 10 and syringe 12, the user can also remove the cap 14 from the needle 10 prior to use of the needle 10 and syringe 12, and can insert the cap 14 into the recess 26. The needle 10 and syringe 12 are then used normally, whereupon the user inserts the needle 10 into the cap 14 in the base 24, such that the user need not risk a needle stick while trying to cap the needle 10.

Once the liquid hardenable solution has been injected into the cap 14 and has encapsulated the needle 10, the needle may be removed from the base 24 and disposed of by traditional means, attending to any traditional biohazardous waste considerations. However, the use of the embodiments of the invention avoids the need of the use of a traditional sharps container, as there is no longer any sharp portion of the medical device (e.g. needle) that is not contained in the hardened liquid hardenable solution. Thus, embodiments of the invention prevent unwanted reuse of medical devices, prevent unwanted needle sticks and other injuries that might transmit pathogens from sharp portions of medical instruments, and reduce or minimize the necessary safe handling procedures.

Since at least some of the materials forming the liquid hardenable solution are liquid, some of the combined material will actually flow into the hollow interior channel of the needle 10. This results in plugging the interior channel further rendering the needle 10 non-reusable.

The admixing of the liquid hardenable solution components causes encapsulation of the needle 10 rapidly, and desirably within a matter of seconds. Useful hardenable solutions are known in the art and include, for example, any liquid resin which when admixed with a liquid resin hardener cures in a sufficiently rapid time to be commercially acceptable for the devices and methods of embodiments of the present invention. For example, an acceptable hardening time may be between about 20 seconds to about 40 seconds. Useful resins include anaerobically curable resins, polyurethane polyacrylate resins, epoxy resins, cyanoacrylates, vinyl resins, silicone resins, and silicone-acrylate resins. Combinations and copolymers of such resin materials are also useful.

For example, useful anaerobically curable resins include those based on mono- and poly(meth)acrylate monomers. Examples of resin hardeners useful with anaerobic curing resins include solutions of metal salts. The use of salt solutions facilitates the mixing of the resin hardener with the hardenable resin to obtain rapid hardening. Virtually any transition metal salt solution may be employed, such as salt solutions of copper, iron, nickel and zinc. Examples of useful copper salts include copper octonate and the diketone salts of copper. Accelerators typically employed with anaerobic systems may also be incorporated in the resin hardener component. Amines are frequently used as accelerators in compatible organic carriers, such as tetraethylene glycol esters. Amines may be effectively combined with saccharin. Hydrazine derivatives and sulfonamides are also useful as accelerators. Useful cyanoacrylate resins may employ amines, thiols, or benzothiazole sulfenamide derivatives as resin hardeners.

Epoxy resins may be used with typical resin hardeners for epoxies, such as amines or thiol compounds. Conventional proportions of resin to resin hardener may be employed, depending on the particular components, as is known in the art.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A containment system for encapsulating a sharp medical instrument comprising:
    a container comprising:
        a rim defining an open end configured to receive a sharp portion of the medical instrument; and
        an ingress port configured to permit injection of a liquid hardenable solution into the container to encapsulate a sharp portion of the medical instrument; and
    a base comprising:
        a recess configured to receive at least a portion of the container distal the rim therein;
        an actuator configured to be contacted by an end of the container distal the rim and to be displaced by continued insertion of the container into the recess; and
        an injection system configured to inject the liquid hardenable solution into the container upon displacement of the actuator.

2. A containment system as recited in claim 1, wherein the container further comprises a compound disposed on an interior surface of the container, the compound being configured to cause hardening of the liquid hardenable solution.

3. A containment system as recited in claim 1, wherein the ingress port is disposed on one of:
    a side of the container;
    a side of the container distal the rim; and
    an end of the container distal the rim.

4. A containment system as recited in claim 1, wherein the ingress port is one of a pair of ingress ports.

5. A containment system as recited in claim 4, wherein each of the ingress ports are located on opposite sides of the container substantially equally distal the rim.

6. A containment system as recited in claim 4, wherein the pair of ingress ports are configured to permit separate components of the liquid hardenable solution to be injected into the container and mixed therein.

7. A containment system as recited in claim 1, wherein the sharp medical instrument is a hypodermic needle.

8. A method for safely and permanently encapsulating a sharp medical instrument, the method comprising:
    inserting the sharp metal instrument into a container, the container comprising:
        a rim defining an open end configured to receive a sharp portion of the medical instrument; and
        an ingress port;
    inserting the container into a base, wherein the base injects a liquid hardenable solution into the container through the ingress port to encapsulate the sharp portion of the medical instrument.

9. A method as recited in claim 8, wherein the container is first inserted into the base, and wherein the sharp portion of the medical instrument is then inserted into the container within the base.

10. A method as recited in claim 8, wherein the sharp portion of the medical instrument is first inserted into the container, and wherein the container containing the sharp portion of the medical instrument is then inserted into the base.

11. A method as recited in claim 8, wherein the base injects the liquid hardenable solution when the container containing the sharp medical instrument is depressed farther into the base than the initial insertion of the container.

12. A method as recited in claim 11, wherein the force of depressing the container injects the liquid hardenable solution.

13. A containment system for encapsulating a hypodermic needle comprising:

a cap comprising:

a rim defining an open end configured to receive the hypodermic needle; and an ingress port configured to permit injection of a liquid hardenable solution into the cap to encapsulate the hypodermic needle; and a base comprising:

a recess configured to receive at least a portion of the cap distal the rim therein;

an actuator configured to be contacted by an end of the cap distal the rim and to be displaced by continued insertion of the cap into the recess; and an injection system configured to inject the liquid hardenable solution into the cap upon displacement of the actuator.

14. A containment system as recited in claim 13, wherein the cap further comprises baffles disposed on an interior surface of the cap to cause mixing of the liquid hardenable solution.

15. A containment system as recited in claim 13, wherein the ingress port is one of a pair of ingress ports.

16. A containment system as recited in claim 15, wherein each of the ingress ports are located on opposite sides of the cap substantially equally distal the rim.

17. A containment system as recited in claim 15, wherein the pair of ingress ports are configured to permit separate components of the liquid hardenable solution to be injected into the cap and mixed therein.

* * * * *